United States Patent
Lafever et al.

(10) Patent No.: US 11,878,154 B2
(45) Date of Patent: *Jan. 23, 2024

(54) NEEDLE SHIELD PULLER FOR DRUG DELIVERY SYSTEM

(71) Applicant: Eli Lilly and Company, Indianapolis, IN (US)

(72) Inventors: Mark Lafever, Indianapolis, IN (US); Andrew Thomas Snow, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,427

(22) Filed: Sep. 2, 2022

(65) Prior Publication Data

US 2022/0409823 A1 Dec. 29, 2022

Related U.S. Application Data (63) Continuation of application No. 16/648,370, filed as application No. PCT/US2018/054594 on Oct. 5, 2018, now Pat. No. 11,452,821.

(Continued)

(51) Int. Cl.
*A61M 5/32* (2006.01)
(52) U.S. Cl.
CPC .................. *A61M 5/3204* (2013.01)
(58) Field of Classification Search
CPC ............. A61M 5/3204; A61M 5/3213; A61M 2005/3215; A61M 5/3202
See application file for complete search history.

(56) References Cited

U.S. PATENT DOCUMENTS

| | | |
|---|---|---|
| 6,585,702 B1 | 7/2003 | Brunel |
| 7,918,824 B2 | 4/2011 | Bishop et al. |

(Continued)

FOREIGN PATENT DOCUMENTS

| | | |
|---|---|---|
| WO | 2003051423 | 6/2003 |
| WO | 07047200 | 4/2007 |

(Continued)

OTHER PUBLICATIONS

Patent Cooperation Treaty International Search Report pertaining to International Application No. PCT/US2018/054594; International Filing Date: Oct. 5, 2018; dated Jan. 8, 2019.

(Continued)

*Primary Examiner* — Katherine H Schwiker
*Assistant Examiner* — Rachel T. Smith
(74) *Attorney, Agent, or Firm* — M. Daniel Spillman (57) ABSTRACT

A device for removing a protective shield such as a needle shield is disclosed. The device includes a cup shaped body with a sidewall, a distal bottom wall and a proximal opening. The protective shield is insertable into the cup shaped body through its proximal opening. Fingers are disposed opposite each other in openings in the sidewall. The fingers are flexibly coupled with the sidewall at a proximal end of the finger and can be resiliently biased inwardly to engage the protective shield. Each finger includes at least one projection for engaging the protective shield. The fingers may also include a distal engagement surface for engaging a lip on the protective shield.

20 Claims, 7 Drawing Sheets

Related U.S. Application Data (60) Provisional application No. 62/571,484, filed on Oct. 12, 2017.

(56) References Cited

U.S. PATENT DOCUMENTS

| | | | |
|---|---|---|---|
| 8,409,138 | B2 | 4/2013 | James et al. |
| 8,734,394 | B2 | 5/2014 | Adams et al. |
| 8,814,828 | B2 | 8/2014 | France |
| 9,044,553 | B2 | 6/2015 | James et al. |
| 9,192,724 | B2 | 11/2015 | Fourt et al. |
| 9,233,212 | B2 | 1/2016 | Holmqvist |
| 9,333,305 | B2 | 5/2016 | McLoughlin et al. |
| 9,402,957 | B2 | 8/2016 | Adams et al. |
| 9,872,961 | B2 | 1/2018 | Fourt et al. |
| 9,913,943 | B2 | 3/2018 | Fourt et al. |
| 10,118,001 | B2 | 11/2018 | Fourt et al. |
| 10,363,377 | B2 | 7/2019 | Atterbury et al. |
| 2008/0228147 | A1 | 9/2008 | David-Hegerich et al. |
| 2012/0238961 | A1 | 9/2012 | Julian et al. |
| 2012/0323177 | A1 | 12/2012 | Adams |
| 2015/0202367 | A1* | 7/2015 | Plaschkes ........... A61M 5/5086 604/154 |
| 2016/0001004 | A1 | 1/2016 | Fourt et al. |
| 2016/0106929 | A1 | 4/2016 | Fournier et al. |
| 2016/0129182 | A1 | 5/2016 | Schuster et al. |
| 2016/0325051 | A1 | 11/2016 | Keim et al. |
| 2016/0346483 | A1 | 12/2016 | Fourt et al. |
| 2017/0224926 | A1 | 8/2017 | Dennis, Jr. et al. |
| 2017/0224929 | A1 | 8/2017 | Sampson et al. |
| 2017/0354779 | A1 | 12/2017 | Atterbury et al. |
| 2019/0009026 | A1 | 1/2019 | Gonzalez et al. |
| 2019/0030249 | A1 | 1/2019 | Gonzalez et al. |
| 2019/0201634 | A1 | 7/2019 | Newton et al. |

FOREIGN PATENT DOCUMENTS

| | | |
|---|---|---|
| WO | 09019439 | 2/2009 |
| WO | 09090499 | 7/2009 |
| WO | 10007395 | 1/2010 |
| WO | 10136076 | 2/2010 |
| WO | 12085580 | 6/2012 |
| WO | 12103140 | 8/2012 |
| WO | 12164403 | 12/2012 |
| WO | 13006119 | 1/2013 |
| WO | 13135566 | 9/2013 |
| WO | 14009705 | 1/2014 |
| WO | 2014037946 | 3/2014 |
| WO | 2014091153 | 6/2014 |
| WO | 2015078869 | 6/2015 |

OTHER PUBLICATIONS

Patent Cooperation Treaty Written Opinion of the International Searching Authority pertaining to International Application No. PCT/US2018/054594; International Filing Date: Oct. 5, 2018; dated Jan. 8, 2019.

* cited by examiner

NEEDLE SHIELD PULLER FOR DRUG DELIVERY SYSTEM

BACKGROUND

The present disclosure relates to a drug delivery system, and in particular to a device for removing a needle shield from a drug delivery system.

Many self-administered injection devices are used with medicament cartridges having needles wherein a needle shield is detachably secured to the cartridge. The needle shield not only protects against accidental needle sticks but also provides protection for the needle against contamination and accidental damage.

For some individuals, such as those whose manual dexterity is limited or compromised, removing such needle shields by hand can be difficult, pose a risk, or simply be an unpleasant task. Specialized devices in the form of needle shield pullers can be used to facilitate the removal of the needle shields.

Figure 4:
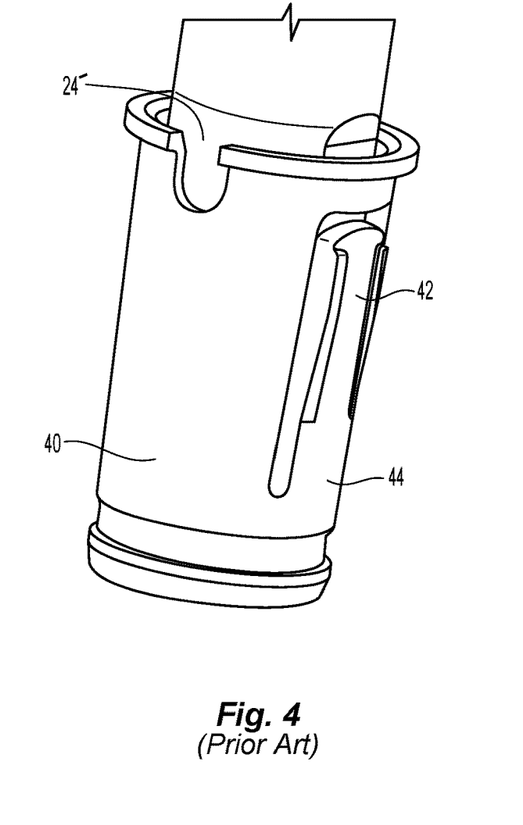
FIG. 4 is a perspective view of a prior art needle shield puller engaged with the needle shield of FIG. 1.
Figure 5:
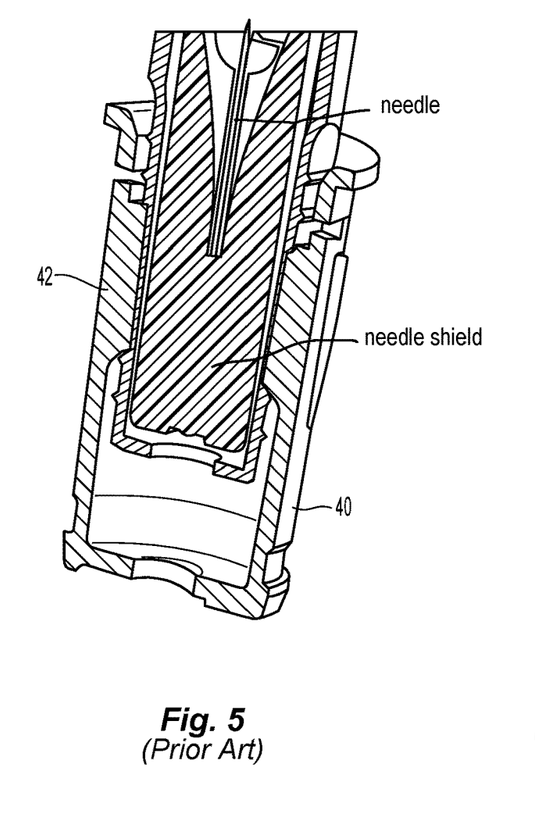
FIG. 5 is a cross sectional view of the prior art needle shield puller and needle shield of FIG. 4.
Figure 6:
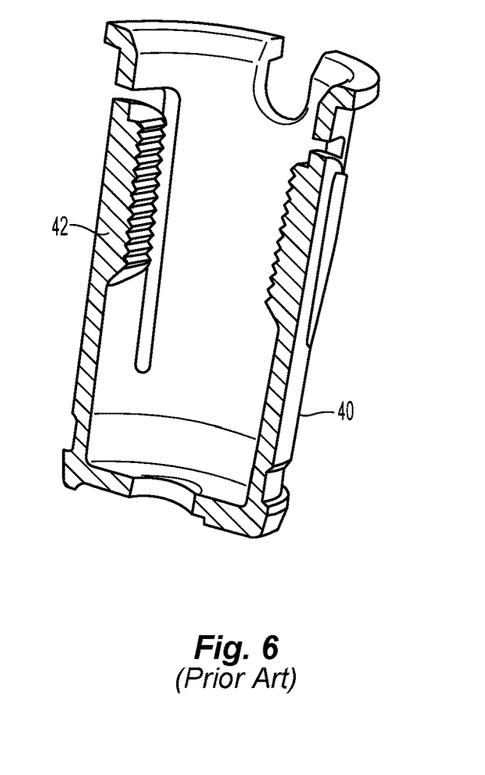
FIG. 6 is a cross sectional perspective view of the prior art needle shield puller of FIG. 4, shown with the needle and the needle shield omitted.

Many of the needle shield pullers are designed to work with only one particular needle shield design or only a limited number of needle shield designs. As a result, manufacturers who provide injection devices that employ a variety of different needle shields may also need to provide a variety of different needle shield pullers to work with the different needle shields. Such a multiplication of parts and inventory is undesirable. Similarly, any patient that self-administers medicament using an injection device may potentially encounter different needle shield designs and require a different needle shield puller for each different needle shield design. A prior art needle shield puller 40 is shown in FIGS. 4-6. Needle shield puller 40 has a cup shaped body that fits over a needle shield 24'. A pair of proximally extending members 42 are flexibly attached at a distal end 44 nearest the base of the cup-shaped body. To remove a needle shield 24', needle shield puller 40 is positioned on the shield 24' and a base cap (not shown) is fit over the puller 40 to press fingers 42 radially inwardly to grip the shield 24'. While fingers 42 are pressed inwardly, the user distally pulls as a unit the base cap, needle shield puller 40 and needle shield 24' gripped therein away from a medicament container to thereby remove the needle shield 24' from the container and needle. While needle shield puller 40 is effective with some needle shields, it is usable only with a limited number of needle shield designs.

SUMMARY

In one form, a device for removing a protective shield is provided. The device includes a cup shaped body defined about a longitudinal axis. The body includes a sidewall circumscribing an interior space and a distal bottom wall, and a proximal opening in communication with the interior space. The proximal opening is configured to receive the protective shield to be disposed within the interior space. The sidewall includes a plurality of sidewall openings formed therein. A plurality of fingers is provided with each having a proximal end flexibly coupled with the sidewall. Each finger extends distally within the corresponding sidewall openings. Each of the fingers further includes at least one projection extending in a circumferential direction and projecting toward the interior space. The at least one projection is engageable with the protective shield when the protective shield is disposed within the interior space.

In another form, a drug delivery system is disclosed. The system includes a drug delivery mechanism including a medicament container, an injection needle in communication with the medicament container, a drive assembly to dispense medicament from the medicament container through the injection needle. A protective shield is disposed about the injection needle. A puller device, such as the one described previously, is configured to remove the protective shield.

BRIEF DESCRIPTION OF THE DRAWINGS

The above mentioned and other features of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. Although the exemplifications set out herein illustrate embodiments of the invention, the embodiments disclosed below are not intended to be exhaustive or to be construed as limiting the scope of the invention to the precise form disclosed.

DETAILED DESCRIPTION

Figure 1:
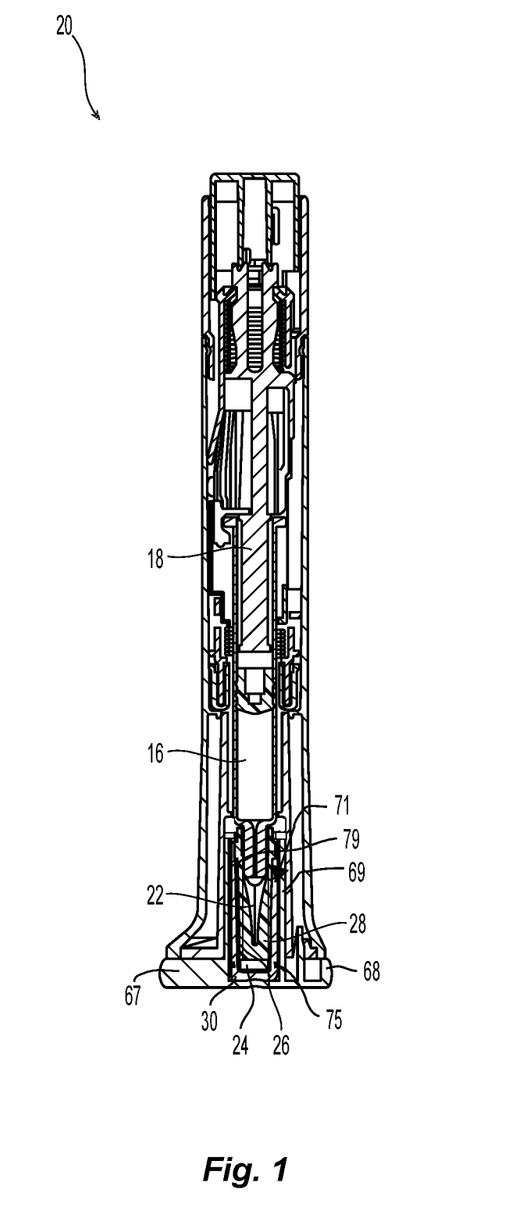
FIG. 1 is a cross sectional view of an injection device having a needle and a needle shield.

Examples of a needle shield puller device and/or drug delivery systems with such needle shield puller devices are disclosed that may be used for convenient removal of a plurality of different needle shield designs from a needle cannula. One of the advantages of the puller device of the present disclosure is to provide a puller device design that is adapted for differently configured rigid needle shields such that manufacturing and inventory costs may be reduced. FIG. 1 provides a cross sectional view of an exemplary drug delivery system 20 in the form of an injection device.

The illustrated system 20 is shown as an automatic injection device (or auto-injector) that, when triggered by the user, automatically inserts a syringe needle into the user and then automatically injects a dose of medication through the needle. However, the device may be a disposable or reusable pen-shaped medication injection device, which is manually handled by a user to selectively set a dose and then to inject that set dose. Injection devices of this type are well known, and the description of device is merely illustrative as the puller device 30 can be adapted for use in variously configured medication delivery devices, including differently constructed pen-shaped medication injection devices, differently shaped injection devices, and infusion pump devices, infusion syringes, and bolus injectors.

System 20 includes assemblies configured to advance a needle 22 and to inject medication through needle 22. In some examples, the assemblies are configured to advance and retract needle 22. Housing of the system defines an injection lumen 21 containing a medicament container 16 that contains a medicament and is in communication with injection needle 22. A drive assembly 18 is operably coupled with container 16 within the injection lumen 21 and causes the dispensing of medicament from container 16 through needle 22 by advancing a piston within container 16. A detailed description of an automatic injection mechanism such as system 20 and drive assembly 18 can be found in U.S. Pat. No. 8,734,394 B2 to Adams et al., which is hereby incorporated herein by reference.

Device 20 may further comprise a medicament. In another embodiment, a system may comprise one or more devices including device 20 and a medicament stored in container 16. The term "medicament" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies including but not limited to IL-23 antibody analogs or derivatives, such as mirikizumab, IL-17 antibody analogs or derivatives, such as ixekizumab, therapeutic agents for pain related treatments, such as galcanezumab, lasmiditan, and any therapeutic agent that is capable of delivery by the above device. The medicament as used in the device may be formulated with one or more excipients. The device is operated in a manner generally as described above by a patient, caregiver or healthcare professional to deliver medicament to a person.

Needle 22 is a syringe needle defining a central passage through which medicament can be injected. Needle 22 is initially covered and protected by a protective shield 24. In the illustrated embodiment, shield 24 protects a needle and is referred to herein as a needle shield. This does not, however, imply that protective shield 24 is limited to protecting needles, as the shield may be operable to protect other sharp or compromiseable elements within a medical device. Needle shield 24 may include a rigid outer housing 26 and/or a resilient flexible material 28 within the inner walls of the housing 26. Material 28 may be rubber, silicone or other suitable material and helps to protect needle 22 from contamination and physical damage. Rigid outer housing 26 also protects needle 22 from physical damage and helps prevent accidental needle sticks.

Prior to performing the initial injection, needle shield 24 is removed from needle 22 from the injection end of the system. Needle shield 24 can be manually removed without the use of any device, however, most users will find it easier and more convenient to remove needle shield 24 with a suitable device such as a puller device 30 illustrated in FIGS. 7-9.

Figure 7:
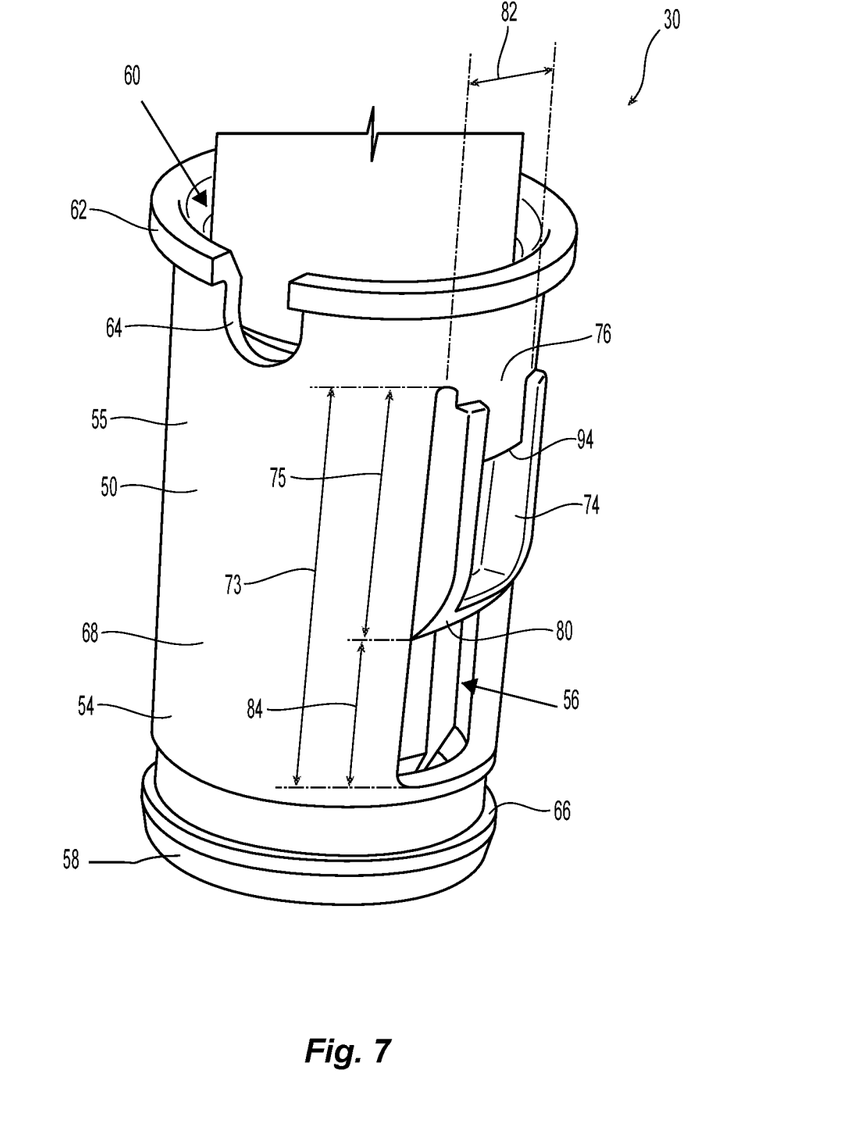
FIG. 7 is a perspective view of an exemplary needle shield puller of the present disclosure engaged with a needle shield.
Figure 8:
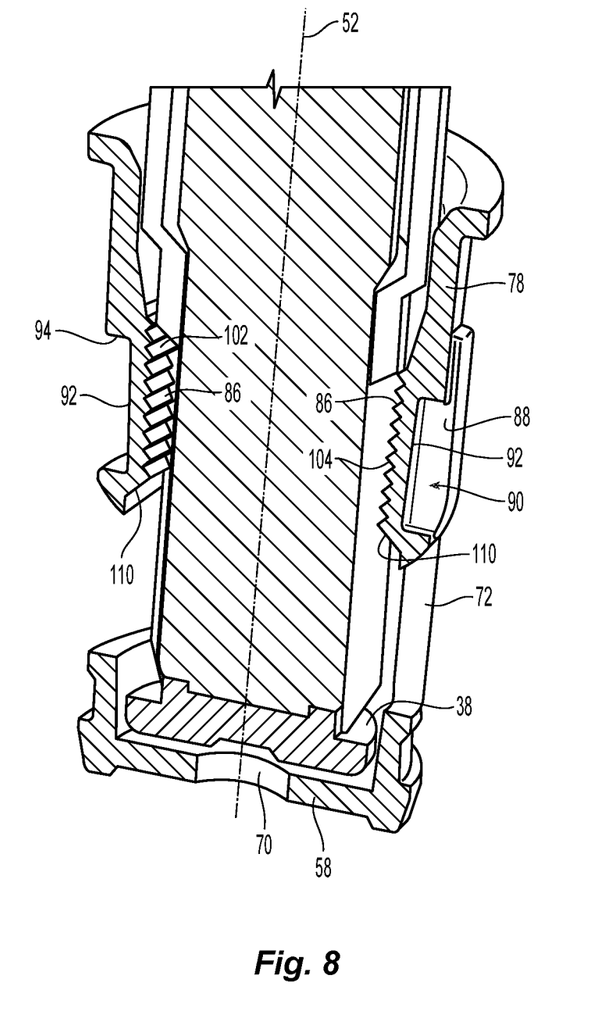
FIG. 8 is a cross sectional perspective view of the needle shield puller and needle shield of FIG. 7.
Figure 9:
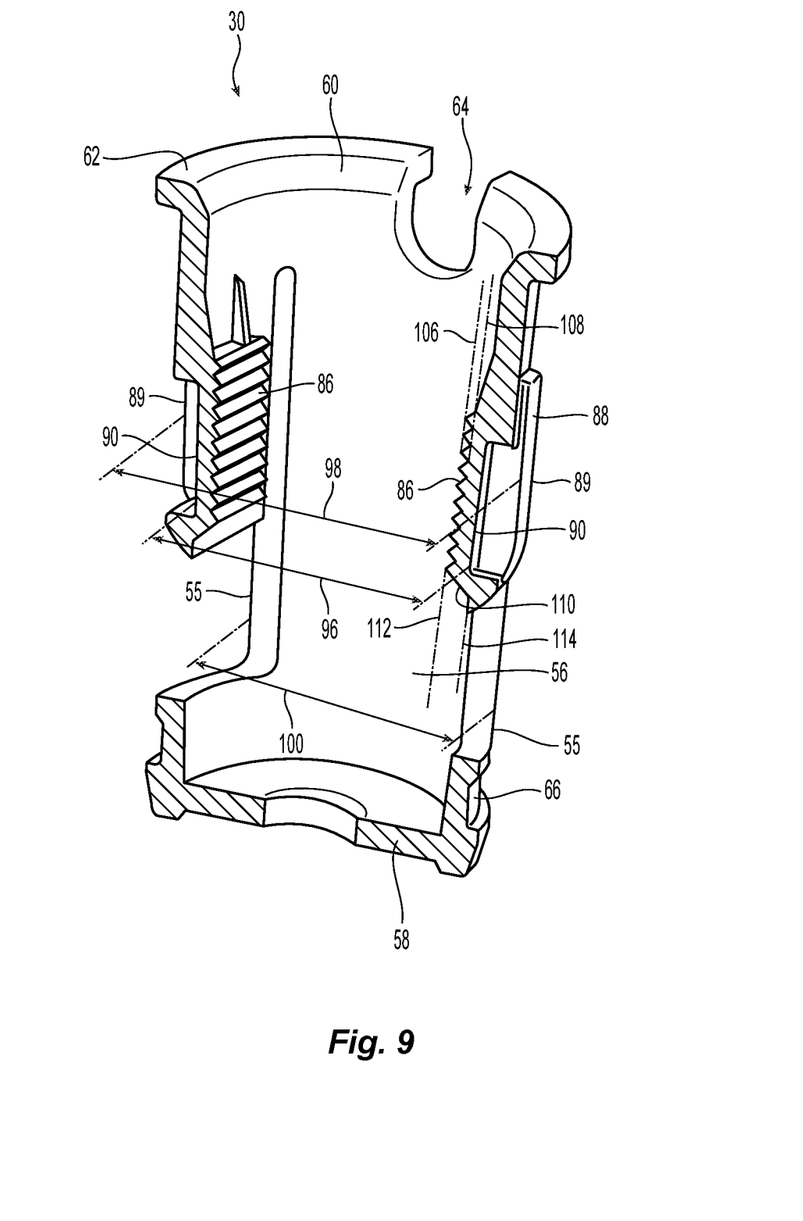
FIG. 9 is a cross sectional perspective view of the needle shield puller of FIG. 7, with the needle shield omitted.

Generally, needle shield 24 is not reattached after the initial removal of shield 24; however, some embodiments may allow shield 24 to be re-attached to cover needle 22. If shield 24 is re-attached, it will need to be removed prior to the next use of needle 22. Device 30 of FIGS. 7-9 is reusable and may be used to remove a re-attached shield 24. When used with a protective shield covering a needle, device 30 may also be referred to as a needle shield puller, however, this label does not imply that device 30 is limited to removing protective shields that cover needles.

It is noted that while an exemplary drug delivery system is depicted in FIG. 1, device 30 of FIGS. 7-9 is not limited to any particular injection device and may be used to remove needle shields employed with other drug delivery mechanisms, either automatic or manual, syringes and other items employing an injection needle. Similarly, it may also be used to remove protective shields used with other, similar items. For example, if protective shields similar to those used with injection needles are used with a lancet or similar item for expressing blood from a patient or any other form of small sharp device, device 30 could be employed with such protective shields.

Figure 2:
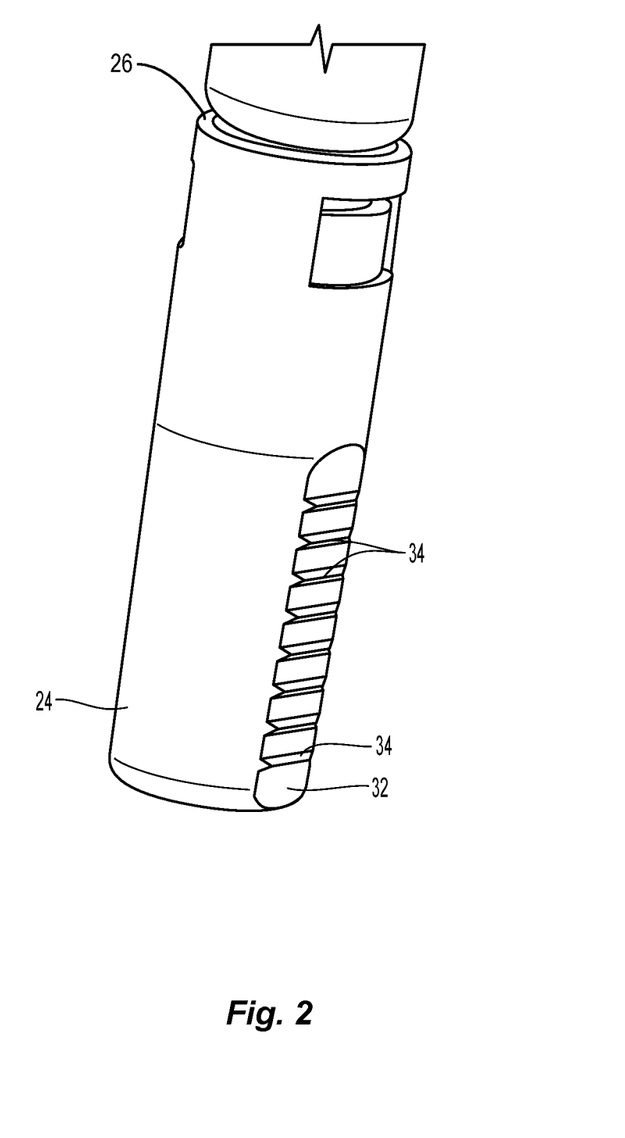
FIG. 2 is a perspective view of one example of a needle shield usable with the device of FIG. 1.

Needle shield 24 is attachable to the medicament container 16 to cover the needle (within the shield housing). As shown in FIG. 2, a first example of the needle shield 24 has rigid outer housing 26 with a generally cylindrical exterior shape. Rigid outer housing 26 also includes two relatively planar axially extending sections 32 on its exterior surface. Sections 32 are located diametrically opposite each other although only one is visible in the view of FIG. 2. Planar sections 32 also include a plurality of parallel projecting ribs 34 that extend laterally perpendicular to the direction of the needle 22 and are disposed longitudinally relative to one another along the needle longitudinal axis. The use of sections 32 with ribs 34 is to provide a more easily gripped surface to facilitate removal of needle shield 24 from container 16 and needle 22.

Figure 3:
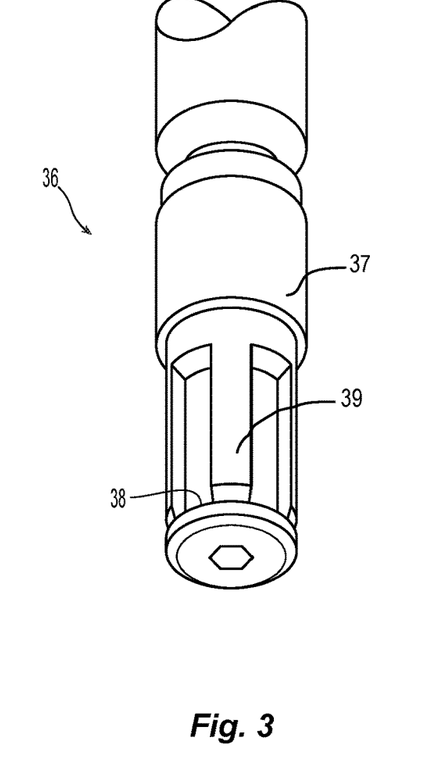
FIG. 3 is a perspective view of another example of a needle shield usable with the device of FIG. 1.

An alternative needle shield 36 is shown in FIG. 3. Needle shield 36 is shown attached to a medicament container and covering the needle (within the shield). As shown in FIG. 3, a second example of the needle shield 36 has a rigid outer housing 37 with a generally cylindrical exterior shape, which may or may not include ribs (shown as a smooth ribless surface). Rigid outer housing also includes longitudinal sections 39 spaced circumferentially from one another. Needle shield 36 includes a projecting radial lip 38 along its bottom distal edge. Projecting lip 38 is coupled to the sections 39 and provides a surface by which needle shield 36 can be grasped or engaged when removing needle shield 36 from container 16 and needle 22.

Device 30, shown in FIGS. 7-9, functions as a protective shield puller and is capable of effectively working with both needle shield 24 and needle shield 36 as well as many other protective shields. Device 30 has a cup shaped body 50 defined about a longitudinal axis 52 (see FIG. 8) that may be coaxial with the needle longitudinal axis. Cup shaped body 50 includes a sidewall 54 that generally circumscribes an interior space 56 and a distal bottom wall 58. A proximal end opening 60 is located opposite distal bottom wall 58 and is in communication with interior space 56 whereby a protective shield can be inserted into interior space 56 through opening 60. Device 30 may include a radially outwardly projecting radial lip 62 extending about opening 60 to enhance the gripability of device 30 to thereby aid in the handling and manual manipulation of device 30. Device 30 may include cut-outs 64 extending axially from the rim of opening 60 to provide more flexibility to device 30 at opening 60. Device 30 may include an annular recess 66 on the exterior surface 68 of sidewall located near the distal bottom wall 58. Recess 66 may be used for secure attachment to a receiving recess of an end plate 67 (shown in FIG. 1) thereby making an integral unit such that the removal of end plate 67 by the user from the injection end of the system removes device 30. The end plate 67 may include a base flange 68 covering the injection lumen of the system 20 and/or an intermediate tubular barrel 69 extending from the base flange 68 into the injection lumen of the system. The sidewall of the tubular barrel defining an axial bore 71 receiving and disposed in a coaxial relationship with the device 30 and the shield 24, with the device coaxially disposed about the shield. The interior surface 79 of the barrel sidewall may include an inner radial flange 75 for mating within the recess 66 of the device 30. Device 30 may include an opening 70 formed in bottom wall 58 about the axis 52 to equalize air pressure between interior space 56 and the ambient environment near bottom wall 58 and to prevent high or low air pressure within interior space 56 from interfering with the insertion or removal of a protective shield.

Sidewall 54 may include a sidewall opening, shown as including two diametrically opposed sidewall openings 72. Device 30 may include a finger 74 located in the sidewall opening 72. In one example, finger 74 is located in each opening 72 and the pair of fingers 74 are located opposite each other relative to interior space 56. Thus, when the interior surface 79 of the barrel sidewall of end plate 67 presses or urges fingers 74 radially inward toward the axis 52 because of their engagement to grip a protective shield, fingers 74 pivot or move toward each other. Each finger 74 is flexibly coupled with sidewall 54 at a proximal hinged end 76 of the finger. Each finger 74 can be resiliently biased into interior space 56.

In the illustrated embodiment, cup shaped body 50 is formed out of a polymeric material using an injection molding process. Each of the fingers 74 is integrally formed with sidewalls 54. Fingers 74 are flexibly coupled with sidewall 54 by a living hinge 78 at the proximal end 76 of finger 74. The distal end 80 of each finger 74 extends freely and is disposed within opening 72.

Openings 72 extend distally beyond the distal end 80 of the finger 74 disposed therein to leave an open gap that allows a user to readily see into interior space 56 and the extent to which the protective shield has been inserted into device 30. Advantageously, this gap is sufficiently large that opening 72 extends distally beyond the distal end 80 of finger 74 by a distance that is at least as great as the circumferential width 82 of finger 74 (see FIG. 7). Reference number 84 represents the distance by which opening 72 extends distally beyond the distal end 80 of finger 74. Reference number 73 represents the axial length of opening 72. Alternatively, distance 84 is at least as great as 50% of the distance 75 between the proximal end 76 and distal end 80 of the finger 74. Even more advantageously, distance 84 satisfies both of these conditions and is at least as great as the larger of the circumferential width 82 of finger 74 and 50% of the distance between finger ends 76, 80.

Each finger 74 may include at least one projection 86 extending laterally in a circumferential direction and projecting radially at a projection tip toward interior space 56. As those having ordinary skill in the art will recognize, a circumferential direction extends along the circumference of cup shaped body 50 or other part in a direction that is perpendicular to axis 52. In the illustrated embodiment, fingers 74 each include a plurality of parallel projections 86 that extend in a circumferential direction.

While projections 86 are potentially capable of gripping most needle shield designs to thereby allow for the removal of the shield, projections 86 can be particularly suited for use with a needle shield such as shield 24 which includes ribs 34 or other irregularities on opposing sides of the shield which can be frictionally, or interlockingly (as preferred) engaged by projections 86. More specifically, when a protective shield is inserted through opening 60 into interior space 56 of device 30, the user can withdraw the end plate 67 that includes the barrel sidewall pressing the bias fingers 74 radially inwardly such that projections 86 engage the protective shield. With projections 86 gripping the protective shield, the user can then pull the protective shield off of the device on which it had been mounted. In some embodiments without end plate 67, the system may be configured such that the user applies an inward radial force to the fingers 74 to grip the shield.

The outwardly facing surface of fingers 74 includes features that enhance the ability of fingers 74 to bias and pivot inwardly. More specifically, each finger includes a pair of radially outwardly projecting and axially extending ridges 88 that are located on opposite circumferential sides of a recess 90. This provides a convenient configuration to strengthen the fingers. The raised ridges 88 are helpful when fingers 74 are depressed radially inwardly. The outer surface of ridges 88 also provide an engagement surface for engaging the inner surface 79 of the barrel. The recess 90 located between ridges 88 provides a space which is capable of receiving the fingertips of the user. Depending upon the manner in which the device 30 is gripped, either or both of ridges 88 and recess 90 will facilitate the handling of the device and depression of fingers 74 into engagement with the protective shield.

In the illustrated embodiment, each recess 90 includes a radially outwardly facing bottom wall 92. Each of the recesses 90 may define a proximal limit 94 that is spaced distally of the proximal end 76 of the finger 94 on which the recess is located. This prevents recess 90 from reducing the thickness of living hinge 78. Sidewall 54 defines an exterior surface 55 that, at each axial location, defines a distance from axis 52. Bottom wall 92 of recess 90 is disposed radially inwardly of exterior surface 55, i.e., at a lesser radial distance from axis 52, while the outwardly facing surfaces 89 on ridges 88 are spaced radially outwardly of exterior surface 55, i.e., at a greater radial distance from axis 52. In other words, at a given axial location, exterior surface 55 of sidewall 54 defines a first diameter 100, the outwardly facing surfaces 89 on ridges 88 defines a second diameter 98, and bottom walls 92 of recesses 90 defines a third diameter 96 wherein the second diameter 98 is greater than the first diameter 100 and the first diameter 100 is greater than the third diameter 96.

As mentioned above, projections 86 are used to engage protective shields. In the illustrated embodiment, each projection 86 includes a proximally facing surface 102 and a distally facing surface 104. In one example, the proximally facing surfaces 102 are all parallel and the distally facing surfaces 104 are all parallel.

Additionally, the projections 86 on each finger 74 define a first radially inner limit 106, i.e., the smallest radial distance from axis 52 defined by one of surfaces 102, 104 of projections 86, and a first radially outer limit 108, i.e., the greatest radial distance from axis 52 defined by one of surfaces 102, 104 of projections 86. The most proximal surface 102 and the most distal surface 104 may be configured to extend beyond the radial inner limit 106 and the radial outer limit 108.

In another example, with reference to FIG. 9, the fingers 74 may include a distally facing engagement surface 110 (as shown) disposed near distal end 80 of the finger. Distally facing engagement surface 110 defines a second radially inner limit 112 and a second radially outer limit 114. The first and second radially inner limits 106, 112 may be equivalent or coextensive as shown. The second radially outer limit 114 may be disposed radially outwardly of the first radially outer limit 108. In other words, distal engagement surface 110 extends radially inward to the same extent as the other projections 86 but the engagement surface 110 extends farther radially outward to a greater distance than projections 86. This configuration of distal engagement surface 110 allows surface 110 to engage a radial lip of a shield, such as for example, lip 38 on protective shield 36 of FIG. 3. The tips of the projections 86 may slidably engage the exterior smooth surface 37 of the shield 36 when the device is being distally withdrawn. Once the distal end 80 of the fingers 74 reaches the annular recess adjacent to the lip 38, the fingers 74 may have a radial inward bias that permits the finger distal end 80 of the fingers to move radially inward into the void defined by the annular recess to position the distal end 74 and engagement surface 110 of the fingers for engagement with the lip 38. In one example, the finger distal end 80 is configured to extend farther radially inward than the opposite finger proximal end 76 that is hingedly attached to allow the position of the finger distal end 80 to engage an engagement feature of the protective shield that is farther radially inward than the finger proximal end 76. The use of device 30 may be with differently configured shields having engagement features on its side such as shield 24 and/or a shield having a distal lip such as shield 36.

In the illustrated embodiment of device 30, on each finger 74, the most distal projection 86 has a distally facing surface that forms the distal engagement surface 110. It is also noted that, in the illustrated embodiment, the second radially outer limit 114 defined by the distally facing engagement surface 110 is disposed radially outwardly of the bottom wall 92 of the recess 90 disposed on the finger 74. In another example, the distal surface, shown as surface 110, of the distalmost projection 86 extends farther radially outward than the distal surface of at least one of the other projections 86. In another example, the distal surface, shown as surface 110, of the distalmost projection 86 extends farther radially outward than the distal surface of the projection 86 proximally adjacent to the distalmost projection.

While the invention has been illustrated and described in detail in the drawings and foregoing description, the same is to be considered as illustrative and not restrictive in character. All changes, equivalents, and modifications that come within the spirit of the invention defined by the claims included herein are desired to be protected.

Various aspects are described in this disclosure, which include, but are not limited to, the following aspects:

1. A device for removing a protective shield, the device comprising a cup shaped body defined about a longitudinal axis, said body having a sidewall circumscribing an interior space and a distal bottom wall, and a proximal opening in communication with the interior space, wherein the proximal opening is configured to receive the protective shield to be disposed within the interior space, wherein the sidewall includes a plurality of sidewall openings formed therein, a plurality of fingers each having a proximal end flexibly coupled with the sidewall and extending distally within the corresponding sidewall openings, each of the fingers further including at least one projection extending in a circumferential direction and projecting toward the interior space, wherein the at least one projection on each finger is engageable with the protective shield when the protective shield is disposed within the interior space.

2. The device of aspect 1 wherein the at least one projection on each finger comprises a plurality of parallel projections extending in a circumferential direction on each finger.

3. The device of any one of aspects 1-2 wherein each of the fingers includes a distal tip end, and the sidewall openings extend distally beyond the distal end of the finger disposed therein by a distance at least as great as the circumferential width of the finger disposed therein.

4. The device of aspect 3 wherein each of the fingers is integrally formed with the sidewalls, and each of the fingers is flexibly coupled with the sidewall by a living hinge, and wherein the sidewall openings extend distally beyond the distal end of the finger disposed therein by a distance that is at least as great as 50% of the distance between the proximal and distal ends of the finger disposed therein.

5. The device of any one of aspects 1-4 wherein each of the fingers has an outwardly facing surface that defines a pair of axial ridges that are disposed on opposite circumferential sides of a recess formed on the outwardly facing surface of the finger, wherein the finger includes a recess wall facing radially outward, the recess wall disposed radially inward relative to an exterior surface of the sidewall adjacent to the axial ridges.

6. The device of aspect 5 wherein the exterior surface of the sidewall defines a first diameter, outwardly facing surfaces of the axial ridges define a second diameter, the recess walls define a third diameter, and wherein the second diameter is greater than the first diameter, and the first diameter is greater than the third diameter.

7. The device of any one of aspects 1-6, wherein the at least one projection on each finger includes a proximally facing surface and a distally facing surface, the proximally and distally facing surfaces defining a first radial inner limit and a first radial outer limit of the at least one projection, wherein each of the fingers further includes a distally facing engagement surface disposed at the distal end of the finger, wherein the distally facing engagement surface defines a second radial inner limit and a second radial outer limit, the second radial outer limit being disposed radially farther than the first radial outer limit.

8. A device for removing a protective shield, the device comprising: a cup shaped body defining an axis and having a sidewall that circumscribes an interior space, a distal bottom wall and a proximal opening in communication with the interior space, the protective shield being insertable into the interior space through the proximal opening; a pair of fingers disposed in openings in the sidewall and located opposite each other relative to the interior space, each of the fingers being flexibly coupled with the sidewall at a proximal end of the finger wherein each finger is resiliently biasable into the interior space; each finger further including a plurality of parallel projections extending in a circumferential direction and projecting toward the interior space whereby the plurality of projections on each finger are grippingly engageable with the protective shield when the protective shield is disposed within the interior space and the pair of fingers are biased inwardly to thereby facilitate the removal of the protective shield; and wherein each of the plurality of projections on each finger includes a proximally facing surface and a distally facing surface, the proximally and distally facing surfaces defining a first radially inner limit and a first radially outer limit of the plurality of projections for each respective finger and wherein each of the pair of fingers further includes a distally facing engagement surface disposed near a distal end of each respective finger wherein the distally facing engagement surfaces define a second radially inner limit and a second radially outer limit for each respective finger, and, for each finger, the first and second radially inner limits are equivalent and the second radially outer limit is disposed radially outwardly of the first radially outer limit.

9. The device of aspect 8 wherein, for each respective finger, the proximally facing surfaces of the plurality of projections are all parallel and the distally facing surfaces of the plurality of projections are all parallel, and wherein the most distal projection on each finger has a proximally facing surface that defines the distally facing engagement surface of the respective finger.

10. The device of aspect 9 wherein the openings in the sidewall extend distally beyond the distal end of the finger disposed therein by a distance at least as great as the greater of the circumferential width of the finger disposed therein and 50% of the distance between the proximal and distal ends of the finger disposed therein, and wherein each of the pair of fingers is integrally formed with the sidewalls whereby each of the pair of fingers is flexibly coupled with the sidewall by a living hinge.

11. The device of any one of aspects 8-10 wherein each of the pair of fingers has an outwardly facing surface that defines a pair of radially outwardly projecting and axially extending ridges that are disposed on opposite circumferential sides of a recess formed on the outwardly facing surface of the finger and wherein the recess having a radially outwardly facing bottom wall that is disposed radially inwardly of an exterior surface of the sidewall.

12. The device of aspect 11 wherein the exterior surface of the sidewall defines a first diameter, outwardly facing surfaces on the ridges defined by the pair of fingers defines a second diameter, the bottom walls of the recesses on the pair of fingers defines a third diameter, and wherein the second diameter is greater than the first diameter and the first diameter is greater than the third diameter and wherein the recesses on the pair of fingers each define a proximal limit that is spaced distally of the proximal end of each respective finger.

13. The device of aspect 12 wherein the openings in the sidewall extend distally beyond the distal end of the finger disposed therein by a distance at least as great as the greater of the circumferential width of the finger disposed therein and 50% of the distance between the proximal and distal ends of the finger disposed therein, and wherein each of the pair of fingers is integrally formed with the sidewalls whereby each of the pair of fingers is flexibly coupled with the sidewall by a living hinge; wherein, for each finger, the proximally facing surfaces of the plurality of projections are all parallel and the distally facing surfaces of the plurality of projections are all parallel, and wherein, for each finger, the most distal projection on the finger has a proximally facing surface that defines the distally facing engagement surface of the finger; and wherein, for each finger, the second radially outer limit defined by the distally facing engagement surface is disposed radially outwardly of the bottom wall of the recess disposed on the finger.

14. A drug delivery system comprising a drug delivery mechanism including a medicament container, an injection needle in communication with the medicament container, a drive assembly for dispensing medicament from the medicament container through the injection needle; a protective shield disposed about the injection needle; and a puller device configured to remove the protective shield, the device comprising: a puller body having a sidewall that circumscribes an interior space about a longitudinal axis, a distal bottom wall interconnected to the sidewall, and a proximal end opening in communication with the interior space, the protective shield being insertable into the interior space through the proximal end opening; a plurality of resilient fingers disposed in openings defined in the sidewall and located opposite each other relative to the interior space, each of the fingers having a finger proximal end flexibly coupled with the sidewall and extending distally toward the distal bottom wall to a finger distal end; and each finger further including at least one projection extending toward the interior space and engaging the protective shield in a manner to facilitate the removal of the protective shield during the removal of the puller device.

15. The system of aspect 14, wherein the at least one projection comprises a plurality of projections disposed along the finger, each of the projections including a proximal surface and a distal surface.

16. The system of aspect 15, wherein the distal surface of a distalmost projection of the plurality of projections of each of the fingers defines a distal engagement surface, the distal engagement surface extends farther radially outward than the distal surface of at least one of the other projections.

17. The system of any one of aspects 14-16, wherein the openings in the sidewall extend distally beyond the finger distal end of the finger disposed therein by a distance at least as great as the greater of a circumferential width of the finger disposed therein and 50% of a distance between the finger proximal and distal ends of the finger disposed therein, and wherein each of the fingers is integrally formed with the sidewalls, wherein the finger proximal end of each finger is flexibly coupled with the sidewall by a living hinge.

18. The system of any one of aspects 14-16, wherein each of the fingers has an outwardly facing surface that defines a pair of axial ridges that are disposed on opposite circumferential sides of a recess defined within the outwardly facing surface of the finger, wherein the recess has a radially outwardly facing bottom wall that is disposed radially inwardly of an exterior surface of the sidewall.

19. The system of aspect 18 wherein the exterior surface of the sidewall at opposing ends defines a first diameter, the outwardly facing surfaces on the axial ridges define a second diameter, the bottom walls of the recesses on the fingers define a third diameter, and wherein the second diameter is greater than the first diameter, the first diameter is greater than the third diameter, and each of the recesses on the fingers defines a proximal limit spaced distally of the proximal end of each respective finger.

20. The system of aspect 19 wherein the openings in the sidewall extend distally beyond the distal end of the finger disposed therein by a distance at least as great as the greater of the circumferential width of the finger disposed therein and 50% of the distance between the finger proximal and distal ends of the finger disposed therein, and wherein each of the fingers is integrally formed with the sidewalls whereby each of the fingers is flexibly coupled with the sidewall by a living hinge; wherein, for each finger, the proximal surfaces of the plurality of projections are all parallel and the distal surfaces of the plurality of projections are all parallel, and wherein, for each finger, the distal surface of the most distal projection on the finger that defines the distally facing engagement surface of the finger; and wherein for each finger, the second radially outer limit defined by the distally facing engagement surface is disposed radially outwardly of the bottom wall of the recess disposed on the finger.

What is claimed is:
1. A device for removing a protective shield from a drug delivery system having a medicament container, an injection needle in communication with the medicament container, a protective shield disposed about said injection needle, the device comprising:
- a puller body having a sidewall that circumscribes an interior space about a longitudinal axis, a distal bottom wall interconnected to the sidewall, and a proximal end opening in communication with the interior space, the protective shield being insertable into the interior space through the proximal end opening, wherein the sidewall defines sidewall openings therein; and
- a plurality of resilient fingers, each resilient finger of the plurality of resilient fingers disposed in a corresponding sidewall opening of the sidewall openings defined in the sidewall, each resilient finger of the plurality of the resilient fingers having a finger proximal end flexibly coupled with the sidewall and extending distally toward the distal bottom wall to a finger distal end,
- wherein each resilient finger of the plurality of resilient fingers further includes at least one projection extending toward the interior space and engaging the protective shield in a manner to facilitate removal of the protective shield during removal of the device.

2. The device of claim 1, wherein the at least one projection comprises a plurality of projections disposed along each resilient finger of the plurality of resilient fingers, each projection of the plurality of projections including a proximal surface and a distal surface.

3. The device of claim 2, wherein the distal surface of a distalmost projection of the plurality of projections of each resilient finger of the plurality of resilient fingers defines a distal engagement surface, the distal engagement surface extends farther radially outward than the distal surface of at least one of the other projections of the plurality of projections.

4. The device of claim 3, wherein the sidewall openings extend distally beyond the finger distal end of the resilient finger of the plurality of resilient fingers disposed therein by a distance at least as great as the greater of a circumferential width of each resilient finger of the plurality of resilient fingers disposed therein and 50% of a distance between the finger proximal and distal ends of each resilient finger of the plurality of resilient fingers disposed therein, and wherein each resilient finger of the plurality of resilient fingers is integrally formed with the sidewall, wherein the finger proximal end of each resilient finger of the plurality of resilient fingers is flexibly coupled with the sidewall by a living hinge.

5. The device of claim 3, wherein each resilient finger of the plurality of resilient fingers has an outwardly facing surface that defines a pair of axial ridges that are disposed on opposite circumferential sides of a recess defined within the outwardly facing surface of each resilient finger of the plurality of resilient fingers, wherein the recess has a radially outwardly facing bottom wall that is disposed radially inwardly of an exterior surface of the sidewall.

6. The device of claim 5, wherein the exterior surface of the sidewall at opposing ends defines a first diameter, each of the axial ridges comprising outwardly facing surfaces that defines a second diameter, the radially outwardly facing bottom walls of the recesses on each resilient finger of the plurality of resilient fingers define a third diameter, and wherein the second diameter is greater than the first diameter, the first diameter is greater than the third diameter, and each of the recesses defined within each resilient finger of the plurality of resilient fingers defines a proximal limit spaced distally of the proximal end of each respective resilient finger.

7. The device of claim 6, wherein the sidewall openings extend distally beyond the distal end of each resilient finger of the plurality of resilient fingers disposed therein by a distance at least as great as the greater of the circumferential width of each resilient finger of the plurality of resilient disposed therein and 50% of a distance between the finger proximal and distal ends of each resilient finger of the plurality of resilient fingers disposed therein, and wherein each resilient finger of the plurality of resilient fingers is integrally formed with the sidewall whereby each resilient finger of the plurality of resilient fingers is flexibly coupled with the sidewall by a living hinge;
- wherein, for each resilient finger of the plurality of resilient fingers, the proximal surfaces of the plurality of projections are all parallel and the distal surfaces of the plurality of projections are all parallel, and wherein, for each resilient finger of the plurality of resilient fingers, the distal surface of the distalmost projection of the plurality of projections on the resilient finger defines the distally facing engagement surface of the resilient finger; and
- wherein, for each resilient finger of the plurality of resilient fingers, a radially outer limit defined by the distally facing engagement surface is disposed radially outwardly of the radially outwardly facing bottom wall of the recess disposed on the resilient finger.

8. The device of claim 1, wherein the puller body comprises a cup-shaped body that is defined by the sidewall and the distal bottom wall.

9. The device of claim 1, wherein the at least one projection comprises a plurality of parallel projections disposed along each resilient finger of the plurality of resilient fingers.

10. The device of claim 9, wherein each of the plurality of parallel projection comprises a proximal surface and a distal surface, wherein the proximal and distal surfaces of each projection of the plurality parallel projections extend between a first radial inner limit and a first radial outer limit, wherein each resilient finger of the plurality of resilient fingers further includes a distally facing engagement surface disposed at the distal end of the resilient finger, wherein the distally facing engagement surface extends between a second radial inner limit and a second radial outer limit, the second radial outer limit being disposed radially farther than the first radial outer limit.

11. The device of claim 1, wherein the sidewall openings extend distally beyond the finger distal end of each resilient finger of the plurality resilient fingers disposed therein by a distance of at least as great as a circumferential width of each resilient finger of the plurality of resilient fingers disposed therein.

12. The device of claim 1, wherein each resilient finger of the plurality of resilient fingers is integrally formed with the sidewall, wherein the finger proximal end of each resilient finger of the plurality of resilient fingers is flexibly coupled with the sidewall by a living hinge.

13. A device for removing a protective shield from a drug delivery system having a medicament container, an injection needle in communication with the medicament container, and a protective shield disposed about said injection needle, the device comprising: a cup shaped body defining an axis and having a sidewall that circumscribes an interior space, a distal bottom wall and a proximal end opening in communication with the interior space, the interior space configured to receive the protective shield through the proximal end opening, the sidewall defining sidewall openings, and a pair of fingers, each finger of the pair of fingers disposed in a corresponding one of the sidewall openings and located opposite each other relative to the interior space, each finger of the pair of fingers being flexibly coupled with the sidewall at a proximal end of each finger of the pair of fingers, each finger of the pair of fingers further including a plurality of projections extending in a circumferential direction in parallel to one another and projecting toward the interior space whereby the plurality of projections on each finger of the pair of fingers are grippingly engageable with the protective shield to thereby facilitate removal of the protective shield, wherein each projection of the plurality of projections on each finger of the pair of fingers includes a proximally facing surface and a distally facing surface, the proximally and distally facing surfaces extending between a first radially inner limit and a first radially outer limit of each projection of the plurality of projections, and wherein each finger of the pair of fingers further includes a distally facing engagement surface disposed near a distal end of each respective finger, wherein each of the distally facing engagement surfaces extends between a second radially inner limit and a second radially outer limit, wherein the second radially outer limit is disposed farther radially outwardly of the first radially outer limit.

14. The device of claim 13, wherein the distally facing surface of a most distal projection on each finger of the pair of fingers defines the distally facing engagement surface of the respective finger.

15. The device of claim 13, wherein the sidewall openings extend distally beyond the distal end of each finger of the pair of fingers disposed therein by a distance at least as great as the greater of a circumferential width of the finger disposed therein or 50% of a distance between the proximal and distal ends of the respective finger disposed therein.

16. The device of claim 13, wherein each finger of the pair of fingers is integrally formed with the sidewall, whereby each finger of the pair of fingers is flexibly coupled with the sidewall by a living hinge.

17. The device of claim 13, wherein each finger of the pair of fingers has an outwardly facing surface that defines a pair of ridges surrounding a recess, the pair of ridges axially extending along opposite circumferential sides of the recess, wherein the recess has a radially outwardly facing bottom wall.

18. The device of claim 17, wherein an exterior surface of the sidewall defines a first diameter, each of the pair of ridges comprises an outwardly facing surface that defines a second diameter, the bottom wall of the recess of each finger of the pair of fingers defines a third diameter, and wherein the second diameter is greater than the first diameter, the first diameter is greater than the third diameter, and wherein the recess of each finger of the pair of fingers defines a proximal limit that is spaced distally of the proximal end of each respective finger.

19. A device for removing a protective shield from a drug delivery system having a medicament container, an injection needle in communication with the medicament container, a protective shield disposed about said injection needle, the device comprising:
 a puller body having a sidewall that circumscribes an interior space about a longitudinal axis, a distal bottom wall interconnected to the sidewall, and a proximal end opening in communication with the interior space, the interior space configured to receive the protective shield through the proximal end opening, wherein the sidewall defines sidewall openings therein;
 a plurality of resilient fingers, each resilient finger of the plurality of resilient fingers disposed in a corresponding sidewall opening of the sidewall openings defined in the sidewall and located surrounding the interior space, each resilient finger of the plurality of the resilient fingers having a finger proximal end flexibly coupled with the sidewall and extending distally toward the distal bottom wall to a finger distal end; and
 each resilient finger of the plurality of resilient fingers further including a plurality of projections axially arranged and extending toward the interior space and engageable with the protective shield in a manner to facilitate removal of the protective shield during removal of said device, each projection of the plurality of projections having a proximal surface and a distal surface, wherein the distal surface of a distalmost projection of the plurality of projections of each respective resilient finger defines a distal engagement surface, the distal engagement surface extends farther radially outward than the distal surface of at least one of the other projections of the plurality of projections.

20. The device of claim 19, wherein each resilient finger of the plurality of resilient fingers has an outwardly facing surface that defines a pair of ridges extending axially and defining a recess therebetween, the pair of axially extending ridges disposed on opposite circumferential sides of the recess, wherein the recess has a radially outwardly facing bottom wall that is disposed radially inwardly of an exterior surface of the sidewall.

\* \* \* \* \*